United States Patent
Shen

(10) Patent No.: US 8,737,699 B2
(45) Date of Patent: May 27, 2014

(54) COMBINATIONAL COMPUTER AIDED DIAGNOSIS

(75) Inventor: Hong Shen, Plainsboro, NJ (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 2307 days.

(21) Appl. No.: 11/188,366

(22) Filed: Jul. 25, 2005

(65) Prior Publication Data

US 2006/0047195 A1    Mar. 2, 2006

Related U.S. Application Data

(60) Provisional application No. 60/606,781, filed on Sep. 2, 2004.

(51) Int. Cl.
*G06K 9/00* (2006.01)

(52) U.S. Cl.
USPC ........... 382/128; 382/130; 382/131; 382/132; 382/276; 382/294

(58) Field of Classification Search
USPC ............... 382/100, 128, 130–132, 276, 294; 128/920, 922, 923; 600/407, 410
See application file for complete search history.

(56) References Cited

U.S. PATENT DOCUMENTS

| | | | | |
|---|---|---|---|---|
| 5,255,187 A * | 10/1993 | Sorensen | ...................... | 600/300 |
| 6,484,047 B1 * | 11/2002 | Vilsmeier | ...................... | 600/407 |
| 6,581,038 B1 * | 6/2003 | Mahran | ............................. | 705/3 |
| 6,904,163 B1 * | 6/2005 | Fujimura et al. | .............. | 382/131 |
| 7,616,799 B2 * | 11/2009 | Ramamurthy et al. | ....... | 382/131 |
| 2002/0039434 A1 | 4/2002 | Levin et al. | | |
| 2002/0141626 A1 * | 10/2002 | Caspi | ........................... | 382/131 |
| 2003/0228042 A1 * | 12/2003 | Sinha | ........................... | 382/131 |
| 2004/0059215 A1 * | 3/2004 | Nishimura et al. | ........... | 600/410 |
| 2005/0065421 A1 * | 3/2005 | Burckhardt | ................... | 600/407 |
| 2005/0105788 A1 * | 5/2005 | Turek et al. | ................... | 382/131 |

FOREIGN PATENT DOCUMENTS

WO        WO 01/5777 A        8/2001

OTHER PUBLICATIONS

"Registration" Defs. 1 & 3. and "Register". Webster's II New Riverside University Dictionary, Riverside Pub Co., c1984, pp. 1-3.*
International Search Report.

* cited by examiner

*Primary Examiner* — Matthew Bella
*Assistant Examiner* — Julian Brooks

(57) ABSTRACT

A computer-implemented method for combinational computer aided diagnosis (C-CAD) includes providing volume data of tissue, providing a database of disease and pathologies, and providing action items for processing the volume data. The method further comprises selecting at least two diseases of interest for the volume data, selecting at least one action item to be performed for each selected disease, determining a set of decision rules based on an output of a selected action item, and producing a combinational report predicting of the tissue of the volume data.

16 Claims, 6 Drawing Sheets

General procedures for anatomy segmentation:
lung, rib, vertebra, vessel tree, airway tree, etc.

Oncology
- Lung cancer: nodule segmentation, volumetrics, detection, registration, and classification
- Bone metastasis: tumor detection and segmentation, fracture detection
- ......
-

Artery diseases:
- Pulmonary embolism: embolism detection and measurement
- Coronary stenosis: .....
- ......

Non-cancer lung diseaes
- Emphysema: .....
- Pneumonia: .....
- ......

Muscuskeletal:
- Osteoporosis: Texture and intensity analysis of trabecular and cortical bones
- Spine stenosis: Spinal cord measurement and shape analysis
- ......

FIG. 5

COMBINATIONAL COMPUTER AIDED DIAGNOSIS

This application claims priority to U.S. Provisional Application Ser. No. 60/606,781, filed on Sep. 2, 2004, which is herein incorporated by reference in its entirety.

BACKGROUND OF THE INVENTION

1. Technical Field

The present invention relates to medical image analysis, and more particularly to a system and method for combinational computer aided diagnosis of disease.

2. Discussion of Related Art

With the development of major anatomical medical modalities (magnetic resonance (MR), computed tomography (CT), . . . ), computer aided diagnosis (CAD) systems are of growing popularity. These modalities create very large amount of data that are tedious and challenging for the physicians to read and interpret.

These major modalities are of high cost. Many insurance agencies require authorizations for diagnostic scans and in most cases do not cover costs for screening purposes. Further, there are concerns about the radiation exposure incurred during a scan with some of the modalities. Because of these concerns the data obtained from a scan is valuable and should be investigated thoroughly.

Given the valuable nature of the volume data radiologists are typically responsible for reporting all abnormalities and pathologies inside the volume data, regardless of the original purpose of the scan. With growing data size, this becomes more and more tedious and in many cases it is difficult to cover all the details.

Given the amount of data in a typical volume, CAD systems do not process a entire scan. Each CAD system only deals with a specific type of pathologies or disease, for instance LungCAD and ColonCAD systems detect lung cancer and colon cancer, respectively.

Therefore, a need exists for a system and method for combinational computer aided diagnosis of disease.

SUMMARY OF THE INVENTION

According to an embodiment of the present disclosure a computer-implemented method for combinational computer aided diagnosis (C-CAD) includes providing volume data of tissue, providing a database of disease and pathologies, and providing action items for processing the volume data. The method further comprises selecting at least two diseases of interest for the volume data, selecting at least one action item to be performed for each selected disease, determining a set of decision rules based on an output of a selected action item, and producing a combinational report predicting of the tissue of the volume data.

Each selected action item detects at least one of the selected diseases of interest. The selected action item quantizes at least one of the selected diseases of interest.

The method further includes storing an instruction set that defines a procedure for carrying out a plurality of selected action items, including the selected action item, sequentially or in parallel. The method further includes selecting an order for performing the plurality of selected action items, wherein the instruction set processes user input and determines a C-CAD procedure.

The method includes providing a user interface listing a plurality of selectable action items.

The selected action item is one of a segmentation, a measurement, a registration, a detection or an evaluation.

According to an embodiment of the present disclosure, a program storage device is provided readable by machine, tangibly embodying a program of instructions executable by the machine to perform method steps for combinational computer aided diagnosis (C-CAD). The method steps including providing volume data of tissue, providing a database of disease and pathologies, and providing action items for processing the volume data. The method further includes selecting at least two diseases of interest for the volume data, selecting at least one action item to be performed for each selected diseases, determining a set of decision rules based on an output of a selected action item, and producing a combinational report predicting of the tissue of the volume data.

According to an embodiment of the present disclosure, a system for combinational computer aided diagnosis (C-CAD) includes a storage component storing disease and pathology information, a sub-computer aided diagnosis module comprising available action items for processing volume data, and a combinational report module for determining a set of decision rules based on an output of the action items and predicting the presence of diseased tissue in the volume data.

The system includes a data splitting module splitting the volume data into a series of sections, each section comprising predicted pathologies.

The system includes a visualization module displaying on a display a combinational report produced by the combinational report module.

BRIEF DESCRIPTION OF THE DRAWINGS

Preferred embodiments of the present invention will be described below in more detail, with reference to the accompanying drawings:

FIG. 5 is a illustration of a infobase for a chest computed tomography (CT) scan according to an embodiment of the present disclosure.

DETAILED DESCRIPTION OF PREFERRED EMBODIMENTS

According to an embodiment of the present disclosure, a framework of a combinational CAD (C-CAD) system detects and measures all pathologies in a volume data. The radiologist's attention will be concentrated on the list of certain locations that are indicated by the system. Further, the system may suggest the detection of disease based on the evaluation of the detected pathologies.

Figure 1:
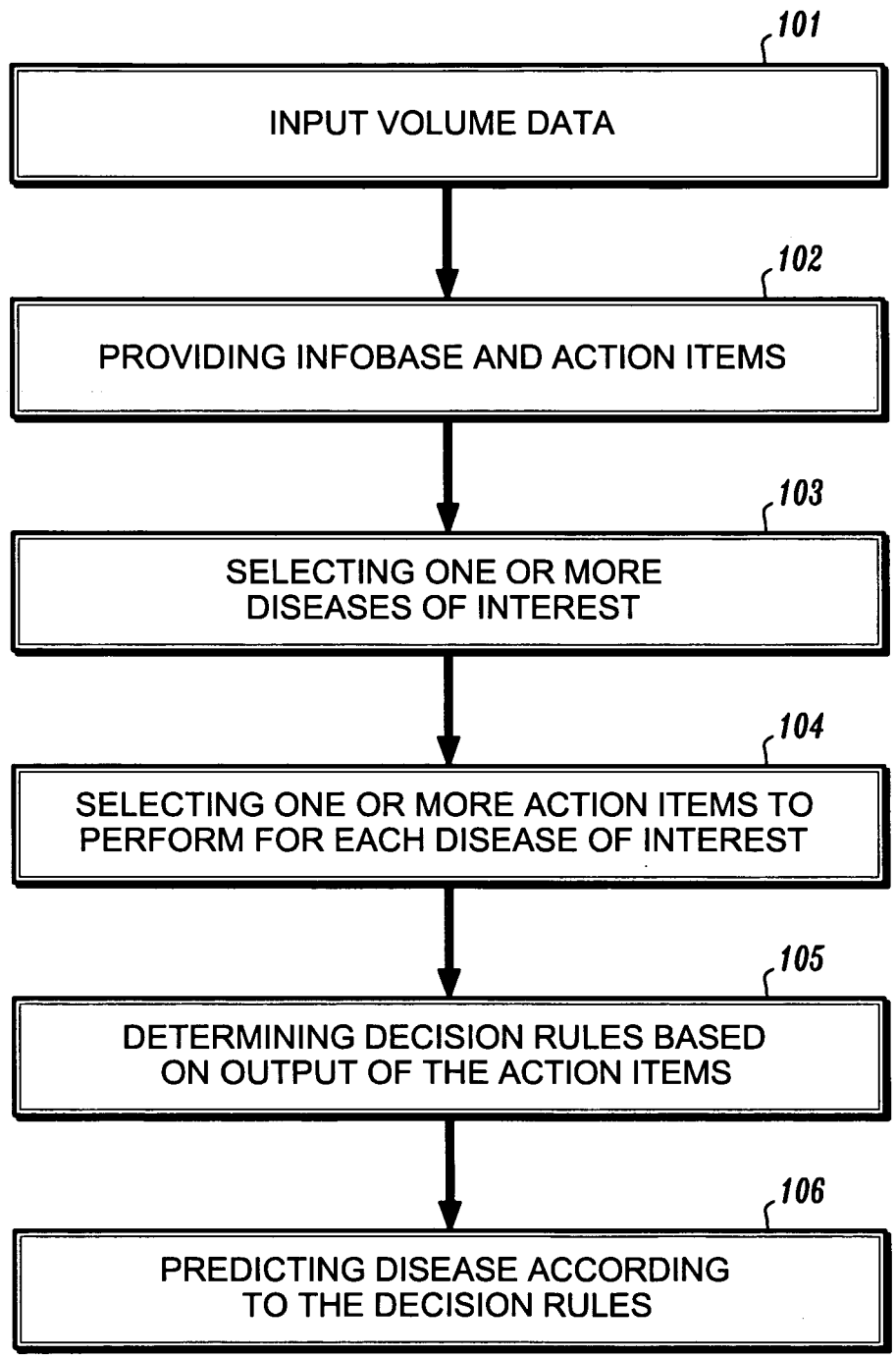
FIG. 1 is a method for combinational computer aided diagnosis (C-CAD) of disease according to an embodiment of the present disclosure.

Referring to FIG. 1, a method for combinational computer aided diagnosis (C-CAD) comprises providing volume data for a patient 101. An InfoBase of disease and pathologies, and action items for processing the volume data are provided 102 by the C-CAD system. A user may select one or more disease of interest for the particular volume data 103. For each disease of interest, one or more action items are selected to be performed 104. A set of decision rules are determined based on the output of the action items 105 and diseased tissue may be predicted/determined in the volume data 106.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 2:
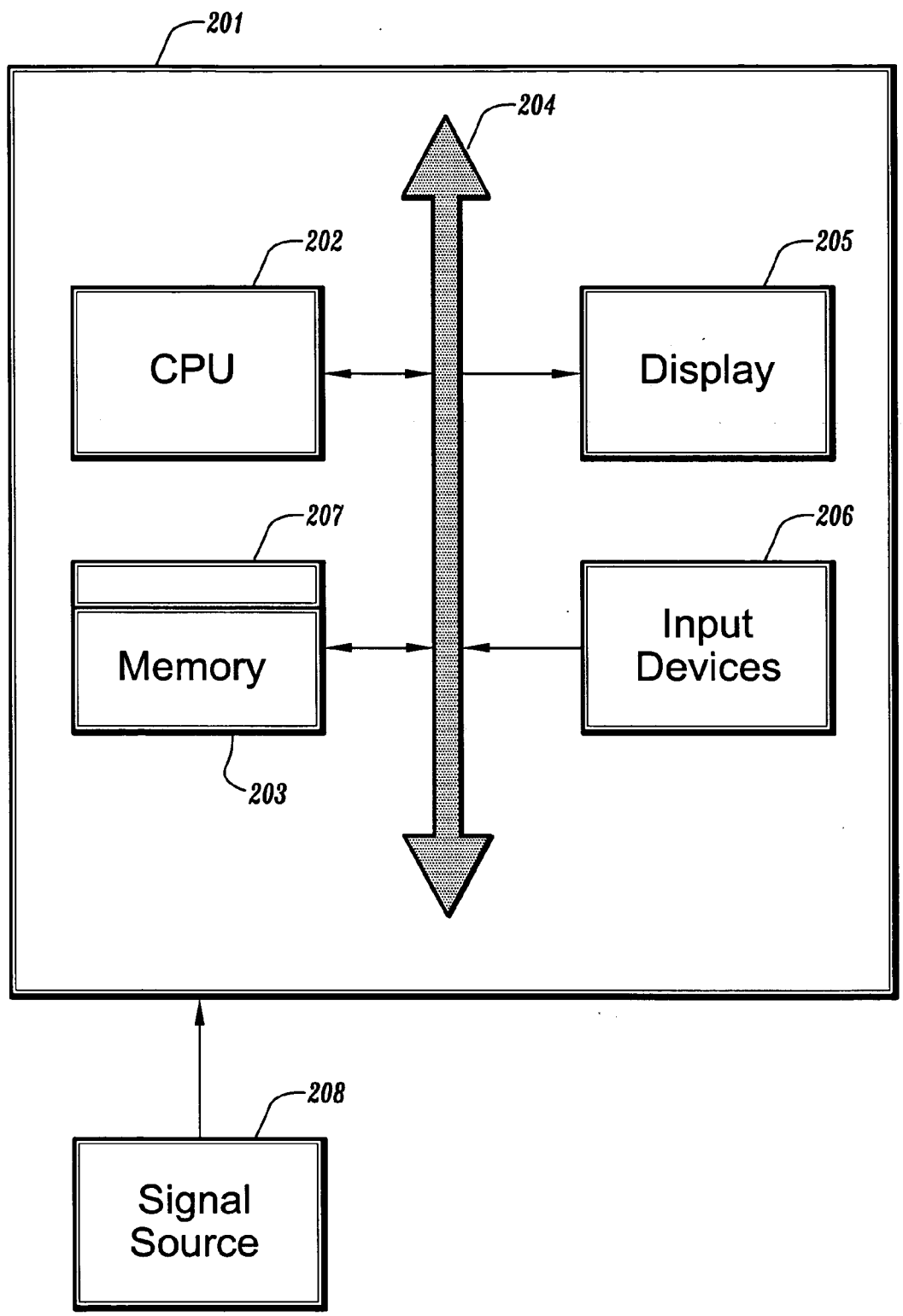
FIG. 2 is a diagram of a system according to an embodiment of the present disclosure.

Referring to FIG. 2, according to an embodiment of the present disclosure, a computer system 201 for implementing a method for C-CAD, inter alia, a central processing unit (CPU) 202, a memory 203 and an input/output (I/O) interface 204. The computer system 201 is generally coupled through the I/O interface 204 to a display 205 and various input devices 206 such as a mouse and keyboard. The display 205 can display views of the virtual volume and registered images. The support circuits can include circuits such as cache, power supplies, clock circuits, and a communications bus. The memory 203 can include random access memory (RAM), read only memory (ROM), disk drive, tape drive, etc., or a combination thereof. The present invention can be implemented as a routine 207 that is stored in memory 203 and executed by the CPU 202 to process the signal from the signal source 208. As such, the computer system 201 is a general purpose computer system that becomes a specific purpose computer system when executing the routine 207 of the present invention.

The computer platform 201 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Figure 3:
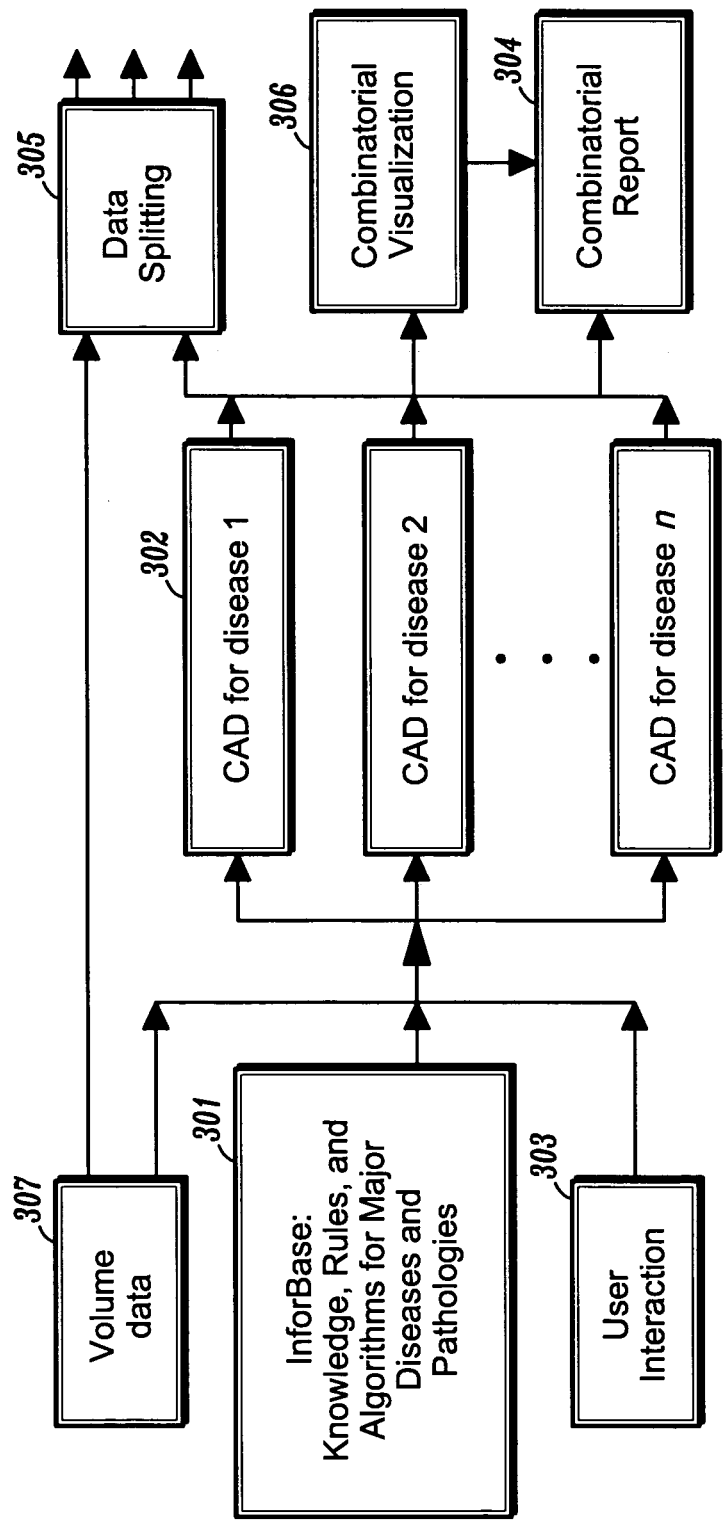
FIG. 3 is a flow chart of a C-CAD according to an embodiment of the present disclosure.

A flow chart for the C-CAD system is shown in FIG. 3. The system includes a storage component 301 or InforBase. The InforBase comprises abstract information groups about major diseases. For each disease, its associated pathologies and/or abnormalities are stored in the InfoBase. Possible action items are stored. The possible action items are preprogrammed algorithm modules, e.g., 302, for detecting and/or quantizing a particular disease. These algorithm modules comprise a sub-CAD system for that disease, which are detailed in FIG. 4.

Beyond these information groups, the system stores an instruction set that defines procedures for carrying out the action items from all sub-CAD systems, either sequentially or in parallel. The system includes a user interface 303 that lists the possible action items, allowing the user to determine which items are to be performed first. An instruction set processes the user input and determines the combinatorial CAD procedures to be performed.

Figure 4:
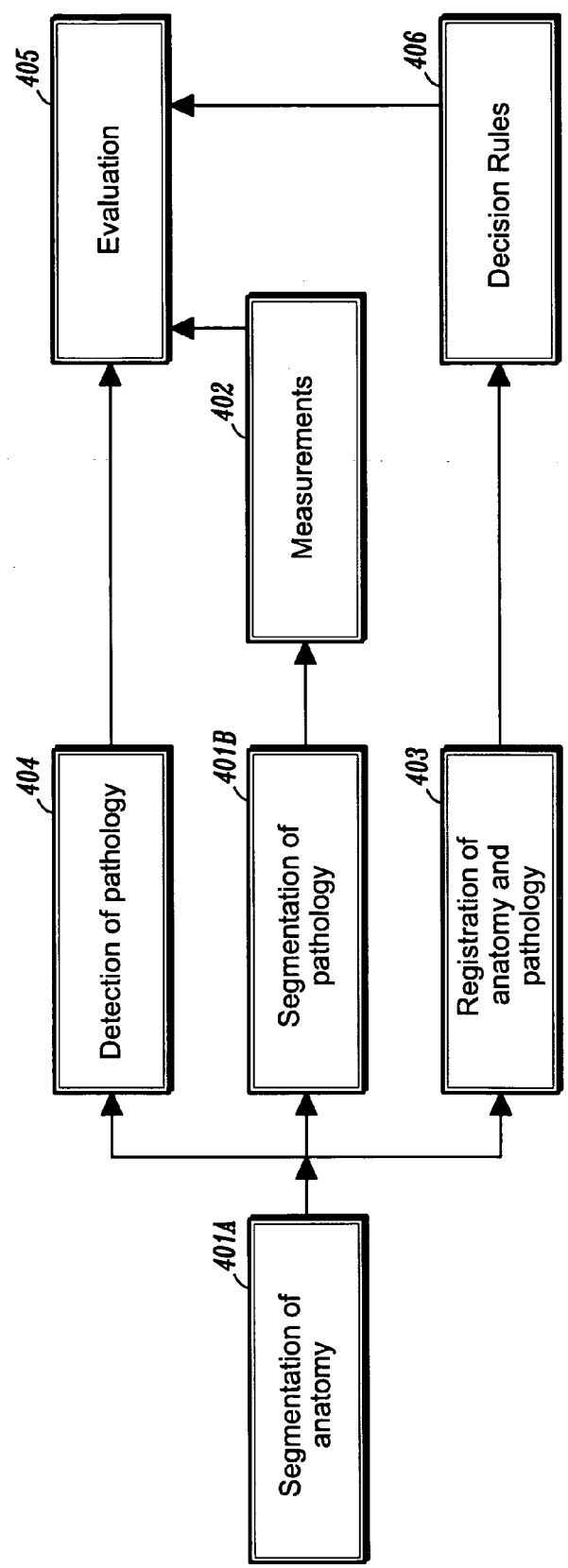
FIG. 4 is a flow chart of action items of a sub-CAD system according to an embodiment of the present disclosure.

For each sub-CAD system as shown in FIG. 4, possible action items include segmentation (401A & 401B), measurement 402, registration 403, detection 404 and evaluation 405. Other possible action items would be obvious to one of ordinary skill in the art in view of the present disclosure.

Segmentation is the basis of all analysis; it isolates the object of interest from the background volume data.

Segmentation of anatomies of interest 401A

Segmentation of abnormalities 401B, such as tumor, lesion, etc.

Measurement 402 includes volume, size measurement, statistical and shape analysis of:

Anatomy of interest

Abnormality of interest

For registration 403, in many situations it is important to track changes in more than one study. This includes Registration of anatomies or tumors in perfusion imaging Registration of anatomies or tumors in two studies over time Detection 404 determines the locations of abnormalities, such as tumors, lesions, deformations, etc.

Evaluation 405, including suggestion and prediction stores in each sub-CAD system a set of decision rules 406.

With the sub-CAD system information, the system uses these decision rules 406 to determine the possibility of a certain disease or to predict the possibility of a future disease.

At the C-CAD system level, several tasks are performed after the action items from the sub-CAD systems are accomplished, including combinational reporting by a combinational report module 304 and splitting and transmission of data by a data splitting module 305.

The combinatorial report module 304 produces a full report containing an evaluation of the general health condition of the patient pertaining to the scanned body section. This report is of visual and interactive nature. The combinatorial report is augmented with built-in visualization tools/module 306 to allow physicians to examine the results with high efficacy and efficiency. The visualization indicates a combination of important pathologies, allowing the user to choose to view some of them in more detail.

The data splitting module 305 automatically splits the volume data 307 into a series of sections, each containing the detected pathologies. Instead of the whole volume that may contain many Gigabytes of data and often put a huge pressure on the network traffic in hospitals, limited and relevant data will be transmitted with the report to the corresponding specialist of the patient.

As an example, shown in FIG. 5 is an InfoBase for a C-CAD system to be used with a chest CT scan. The sub-CAD systems include general segmentation of anatomies as well as modules that detect a set of major pathologies associated with the major diseases inside the chest.

Figure 6:
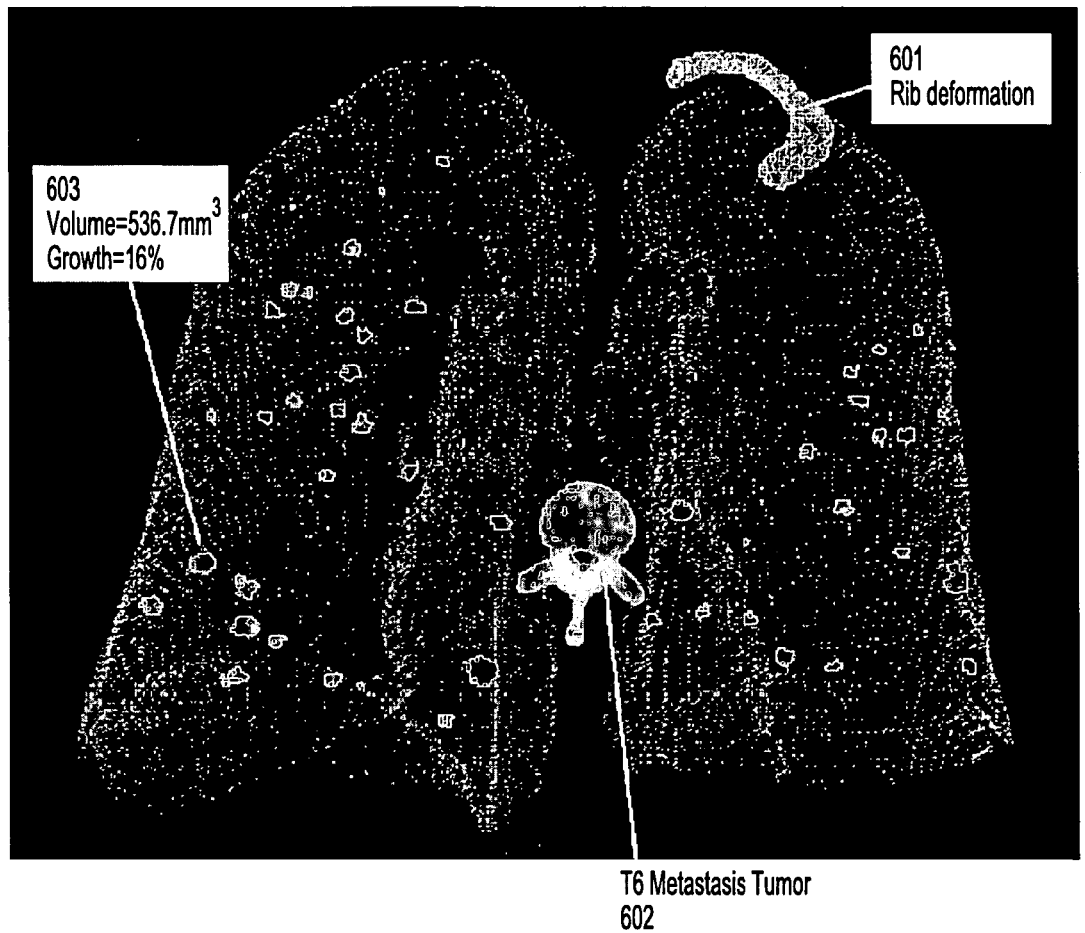
FIG. 6 is an illustration of a combinational visualization according to an embodiment of the present disclosure.

The visualization is an active component of the combinatorial report. It is important that the combined information is rendered in a most effective fashion, yet in a limited display space. Shown in FIG. 6 is an example of such visualization. All the detected lung nodules are rendered in surface rendering, with its actual size and shape, along with the lung surface as a reference. The rib and vertebra with pathology are also rendered in volume rendering and surface rendering, whichever best presenting the abnormality. The user could choose to see more information in the display window, for instance, the complete thoracic cage, or the vessel tree, airway tree etc. In the limited display window, however, the system will render the most relevant information to the user.

FIG. 6 is an example of combinatorial visualization as an integral part of the combinatorial report. This is a 3D display of the abnormalities, including a rib deformation 601, a T6 metastasis tumor 602 and a volume 603 having a growth pattern outside a normal range. The user can rotate and zoom to see the locations of interest. Only relevant anatomies are shown. The normal anatomies are removed to prevent blocking. Brief annotations are shown in top of the display. When the view is changed by the user, the annotations will update themselves to point to the correct location. From this we see three highlights—a grown lung nodule, a metastasis tumor in the vertebra, and a deformation on one of the ribs. This display is linked to the main window displaying volume data. A click on the abnormality will update the main window to the corresponding location in the volume data.

The concept or framework of the C-CAD system can add in the need for preventive healthcare and the high cost of a medical study and the study of large volume data. The system and method integrate with available and future CAD modules in a systematical way. That is, CAD modules according to an embodiment of the present disclosure can be used as sub-CAD systems, being stored with instruction procedures in a system level "InforBase". The results can be rendered as a combinatorial report, in which all the information will be presented in a most effective and efficient way. Particularly, the report can be augmented with interactive visualization. The construction of the C-CAD system is incremental, which is practical for implementation, starting with the current available modules and integrating additional sub-CAD system as they become available.

According to an embodiment of the present disclosure, a system and/or method may be implemented for a specific area of a patient's anatomy, e.g., chest. For example, given a CT chest scan, the system and method predict the presence of multiple diseases, e.g., disease of the lung, heart and surrounding bone. The prediction of multiple diseases may be performed even where a concerned physician is seeking data on one particular disease.

According to an embodiment of the present disclosure, a system and/or method receives a scan covering multiple areas of a patient, e.g., chest, pelvis, legs, etc., predicts the presence of multiple diseases within the scan and splits the scan and an analysis according to the multiple areas. The splitting is performed by the data splitter 305 according to given areas, for example, user determined dimensions of a chest area to be analyzed. An analysis/prediction about a given area, e.g., pelvis, is then delivered to appropriate personnel or equipment for further study. For example, a physician who specializes in ear, nose and throat will not receive an analysis and a portion of a scan related to a chest. According to an example, prediction data may be sent to a database. Thus, by delivering a reduced data set, e.g., scan and analysis of a chest area from a scan of an entire body, a time for delivery of the analysis and bandwidth use over a network for delivering the analysis may be reduced.

Having described embodiments for a system and method for C-CAD, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A computer-implemented method for combinational computer aided diagnosis (C-CAD) comprising:
receiving volume data of tissue;
receiving a database of disease and pathologies;
receiving action items for processing the volume data;
receiving a selection of at least two diseases of interest for the volume data;
segmenting images of an object of interest corresponding to each of the diseases of interest from the volume data;
receiving a selection of at least one action item to be performed on the volume data for each selected disease, wherein the at least one selected action item performs a registration of segmented images of the objects of interest to the volume data;
determining, by a processor, a set of decision rules corresponding to respective ones of the selected diseases based on the registration, wherein the sets of decision rules are rules for detecting changes in the tissue over time when the registration is determined for the tissue over time;
evaluating the volume data of the tissue using the sets of decision rules; and
producing, by the processor, a combinational report including predictions of a presence of each of the at least two diseases of interest in the tissue of the volume data.

2. The computer-implemented method of claim 1, wherein each selected action item detects at least one of the selected diseases of interest.

3. The computer-implemented method of claim 1, wherein the selected action item quantizes at least one of the selected diseases of interest.

4. The computer-implemented method of claim 1, further comprising storing an instruction set that defines a procedure for carrying out a plurality of selected action items, including the selected action item, sequentially or in parallel.

5. The computer-implemented method of claim 4, further comprising receiving a selection of an order for performing the plurality of selected action items, wherein the instruction set processes user input and determines a C-CAD procedure.

6. The computer-implemented method of claim 1, further comprising providing a user interface listing a plurality of selectable action items.

7. The computer-implemented method of claim 1, wherein the at least one selected action item further includes one of a measurement, a detection or an evaluation.

8. The computer-implemented method of claim 1, wherein the volume data of tissue include different tissue types and the at least two diseases of interest effect different tissue types, wherein the combinational report includes predictions of a presence of each of the at least two diseases of interest in the different tissue types of the volume data.

9. A non-transitory computer readable medium embodying instructions executed by a processor to perform method steps for combinational computer aided diagnosis (C-CAD), the method steps comprising:
receiving volume data of tissue;
receiving a database of disease and pathologies;
receiving action items for processing the volume data;
receiving a selection of at least two diseases of interest for the volume data;
segmenting images of an object of interest corresponding to each of the diseases of interest from the volume data;
receiving a selection of at least one action item to be performed on the volume data for each selected disease, wherein the at least one selected action item performs a registration of segmented images of the objects of interest to the volume data;
determining a set of decision rules corresponding to respective ones of the selected diseases based on the registration, wherein the sets of decision rules are rules for detecting changes in the tissue over time when the registration is determined for the tissue over time;

evaluating the volume data of the tissue using the sets of decision rules; and producing a combinational report including predictions of a presence of each of the at least two diseases of interest in the tissue of the volume data.

10. The non-transitory computer readable medium of claim 9, wherein each selected action item detects at least one of the selected diseases of interest.

11. The non-transitory computer readable medium of claim 9, wherein the selected action item quantizes at least one of the selected diseases of interest.

12. The non-transitory computer readable medium of claim 9, further comprising storing an instruction set that defines a procedure for carrying out a plurality of selected action items, including the selected action item, sequentially or in parallel.

13. The non-transitory computer readable medium of claim 12, further comprising receiving a selection of an order for performing the plurality of selected action items, wherein the instruction set processes user input and determines a C-CAD procedure.

14. The non-transitory computer readable medium of claim 9, further comprising providing a user interface listing a plurality of selectable action items.

15. The non-transitory computer readable medium of claim 9, wherein the at least one selected action item further includes one of a measurement, a detection or an evaluation.

16. The non-transitory computer readable medium of claim 9, wherein the volume data of tissue include different tissue types and the at least two diseases of interest effect different tissue types, wherein the combinational report includes predictions of a presence of each of the at least two diseases of interest in the different tissue types of the volume data.

* * * * *